(12) United States Patent
Caldwell

(10) Patent No.: US 8,357,914 B1
(45) Date of Patent: Jan. 22, 2013

(54) UV DISINFECTING APPARATUS

(75) Inventor: Dawn E. Caldwell, Evensville, TN (US)

(73) Assignee: Dawn E. Caldwell, Evensville, TN (US)

( * ) Notice: Subject to any disclaimer, the term of this patent is extended or adjusted under 35 U.S.C. 154(b) by 0 days.

(21) Appl. No.: 13/134,992

(22) Filed: Jun. 22, 2011

Related U.S. Application Data

(60) Provisional application No. 61/359,125, filed on Jun. 28, 2010.

(51) Int. Cl.
  *A61L 2/10* (2006.01)
(52) U.S. Cl. .................. 250/455.11; 250/504 R; 422/24; 422/121; 422/186.3
(58) Field of Classification Search ............. 250/455.11; 422/24, 121, 186.3
See application file for complete search history.

(56) References Cited

U.S. PATENT DOCUMENTS

| | | | | |
|---|---|---|---|---|
| 3,433,579 A | * | 3/1969 | Runnion ..................... 312/209 |
| 4,772,795 A | * | 9/1988 | Sakurai et al. ........... 250/455.11 |
| 4,990,313 A | * | 2/1991 | Pacosz ........................... 96/224 |
| 5,112,370 A | * | 5/1992 | Gazzano ...................... 422/121 |
| 5,891,399 A | * | 4/1999 | Owesen ........................ 422/121 |
| 5,900,212 A | * | 5/1999 | Maiden et al. .................. 422/24 |
| 6,039,928 A | * | 3/2000 | Roberts ...................... 422/186.3 |
| 6,190,078 B1 | * | 2/2001 | Smith ........................... 401/195 |
| 6,576,188 B1 | * | 6/2003 | Rose et al. ...................... 422/20 |
| 6,797,042 B2 | | 9/2004 | LaFerriere et al. |
| 7,238,326 B2 | * | 7/2007 | Zhang ........................... 422/121 |
| RE40,022 E | * | 1/2008 | Fencl et al. ................... 422/121 |
| 7,888,657 B1 | * | 2/2011 | Zadro ...................... 250/455.11 |
| 8,058,629 B2 | * | 11/2011 | Long ........................ 250/455.11 |
| 2003/0217641 A1 | * | 11/2003 | Palestro et al. ................. 95/273 |
| 2004/0256581 A1 | | 12/2004 | Au et al. |
| 2006/0079948 A1 | | 4/2006 | Dawson |
| 2006/0175554 A1 | * | 8/2006 | Riddell .................... 250/455.11 |
| 2012/0074334 A1 | * | 3/2012 | Milligan ................. 250/455.11 |

\* cited by examiner

*Primary Examiner* — David A Vanore

(57) ABSTRACT

A disinfecting apparatus comprises a housing, an ultraviolet (UV) light, and a dispensing mechanism. The housing is designed to receive contaminated pens and dispense disinfected pens. The UV light comprises a UVC cold cathode light bulb housed integrally within the housing and an AC power connector. In a preferred embodiment the AC power connector further comprises an ON/OFF switch which controls the UV light bulb. The dispensing means comprises a means of re-obtaining a pen from the housing for subsequent use. Between uses, the pens are immersed in the light of the UV light bulb which helps to kill bacteria and germs associated with illnesses commonly contracted in such public places.

2 Claims, 2 Drawing Sheets

UV DISINFECTING APPARATUS

CROSS REFERENCE TO RELATED APPLICATION

This application claims priority to provisional application No. 61/359,125 filing date Jun. 28, 2010 title of invention UV Disinfecting Apparatus

FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The field of the invention relates generally to article disinfecting apparatus and more particularly, to an ultraviolet disinfecting apparatus for shared writing utensils.

SUMMARY OF THE INVENTION

In recent society, there has been a trend toward increased sanitization of everyday objects and surfaces that one tends to come in contact with. This trend is evidenced by a quick trip to one's local store, where one will find the shelves lined with antibacterial soap, hand lotion, sanitizer, antibacterial surface cleaner, HEPA air filtration systems and the like. At the same time Methicillin-Resistant *Staphylococcus aureus* (MRSA) has become a bacterium responsible for hard to treat infections in humans. It has evolved an ability to resist conventional treatment with antibiotics, including penicillin, methicillin and others. The past decade has seen a significant increase in the occurrence of MRSA infections. Various studies have shown that the number of MRSA infections treated in hospitals has doubled from 1995 to 2005. Other findings suggest that MRSA infections are responsible for more deaths in the U.S. each year than AIDS. Accordingly, there exists a need for a means by which the MRSA bacterium, FLU virus and other germs can be quickly and easily removed from everyday surfaces. The development of the present invention fulfills this need.

A UV disinfecting apparatus is a container for holding shared writing utensils having an integral ultraviolet (UV) light to help kill germs and bacteria. Upon initial observation, the apparatus appears as a conventional pen holder that is placed on a counter for general public use at a hospital, bank, post office, doctor's office, or the like. However after closer inspection, it can be seen that the interior of the holder is provided with a central ultraviolet lamp. The lamp is powered by an electrical cord that plugs into the wall and controlled through a switch mounted on the cord. Thus, as each pen is placed in the container after use, it is bathed in an encompassing UV light which kills any germs and bacteria that may have been deposited on the pen or writing utensil during use. As such germs that cause infections, illnesses, the flu, and common colds are killed quickly and the pen is left in the cleanest state possible for the next user. The use of the present apparatus allows for the sterilization and cleaning of publicly used writing utensils in a manner that is quick, easy, and effective.

DESCRIPTION OF DRAWINGS

The advantages and features of the present invention will become better understood with reference to the following more detailed description and claims taken in conjunction with the accompanying drawings, in which like elements are identified with like symbols and in which:

DESCRIPTIVE KEY

Figure 1:
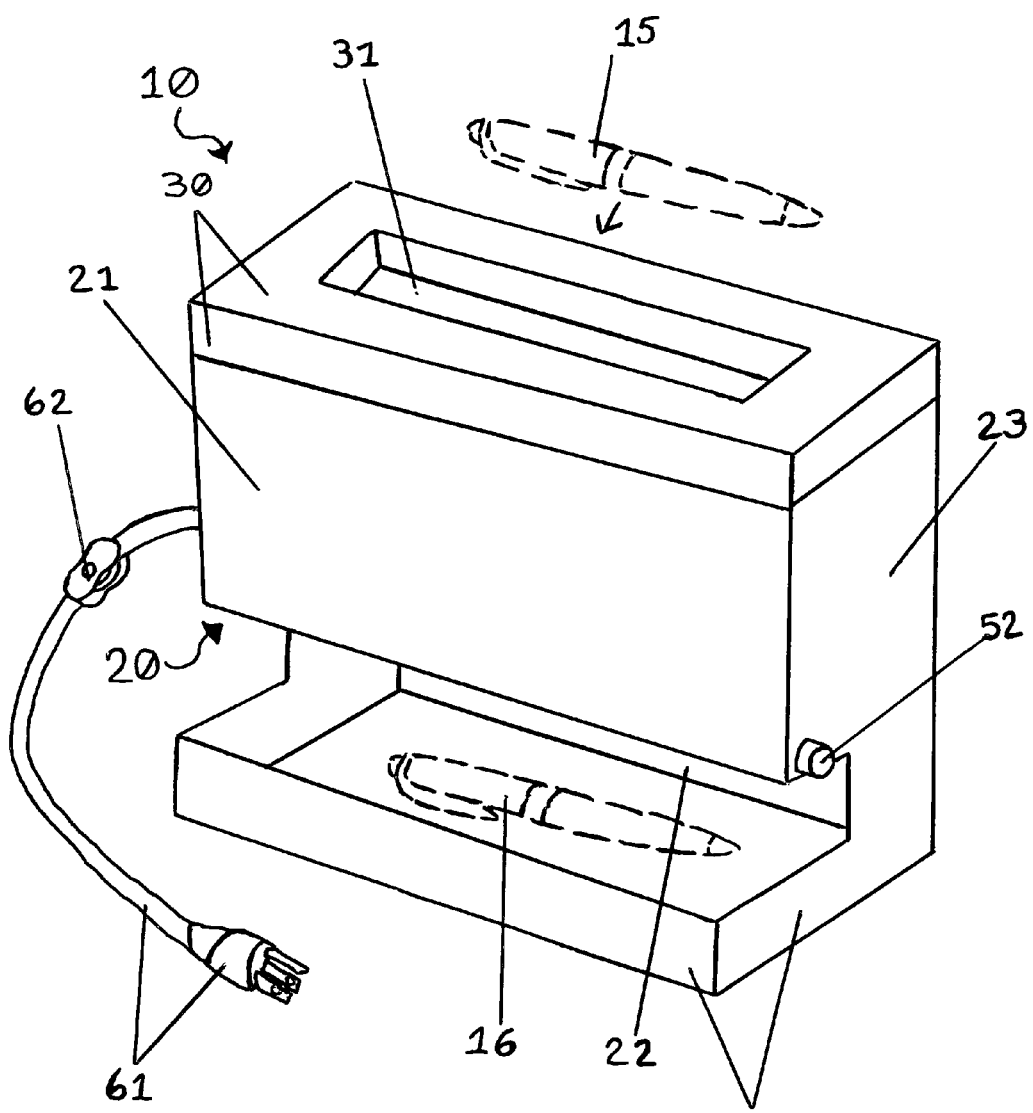
FIG. 1 is a perspective view of a UV disinfecting apparatus 10, according to a preferred embodiment of the present invention; and, FIG. 2 is another perspective view of the UV disinfecting apparatus 10, according to a preferred embodiment of the present invention.

10 UV disinfecting apparatus
15 contaminated writing utensil
16 disinfected writing utensil
20 enclosure
21 front panel
22 rear panel
23 side panel
24 tray
30 lid
31 slot
32 barricade
40 guide panel
50 rolling dispenser
51 groove
52 handle
60 light
61 power cord
62 switch

DETAILED DESCRIPTION OF THE INVENTION

Figure 2:
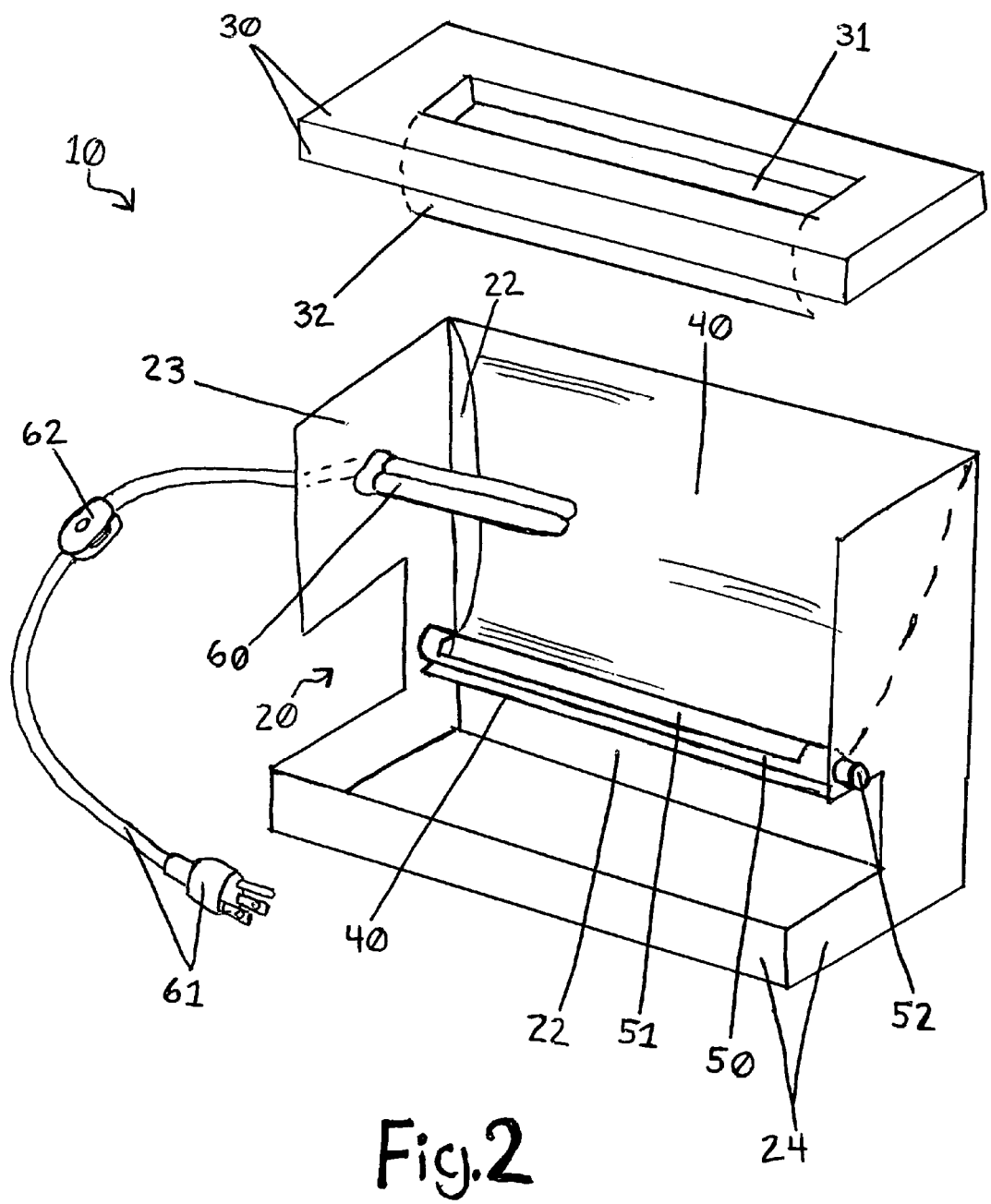

The best mode for carrying out the invention is presented in terms of its preferred embodiment, herein depicted within FIGS. 1 and 2. However, the invention is not limited to the described embodiment, and a person skilled in the art will appreciate that many other embodiments of the invention are possible without deviating from the basic concept of the invention and that any such work around will also fall under the scope of this invention. It is envisioned that other styles and configurations of the present invention can be easily incorporated into the teachings of the present invention, and only one particular configuration shall be shown for purposes of clarity and disclosure and not by way of limitation of scope.

The terms "a" and "an" herein do not denote a limitation of quantity, but rather denote the presence of at least one of the referenced items.

The present invention describes a UV disinfecting apparatus (herein described as the "apparatus") 10, which provides a means to eradicate microscopic organisms on a contaminated writing utensil 15 which may comprise items such as, but not limited to: a pen, pencil, or the like. The apparatus 10 is envisioned to be utilized in locations heavily trafficked with individuals who utilize public writing utensils which may transfer airborne illness or various other contagious sicknesses such as hospitals, banks, post offices, or the like. The apparatus 10 enables and individual to place a contaminated writing utensil 15 into an enclosure 20 and enable said contaminated writing utensil 15 to be sterilized for subsequent use. The apparatus 10 is particularly suited for eradicating microscopic organisms with UVC radiation.

Referring now to FIG. 1, a perspective view of the apparatus 10, according to the preferred embodiment of the present invention, is disclosed. The apparatus 10 comprises a rectangular enclosure 20 which provides a means to insert a contaminated writing utensil 15 for sterilizing. The enclosure 20 comprises a front panel 21, a rear panel 22, a pair of side panels 23, and a tray 24. The enclosure 20 houses an internal means of sanitizing (see FIG. 2) and provides a means of displaying the apparatus 10 for use. The apparatus 10 is envisioned to be placed on a level surface such as a desk or other location accessible to various users. The enclosure 20 is envisioned to be fabricated from materials such as, but not limited to: plastic, metal or the like. It is envisioned for each panel 21, 22, 23, and the tray 24 to be integrally molded, yet other attachment means may be utilized without limiting the scope of the apparatus 10.

The tray 24 extends outwardly below the front panel 21 and provides a shallow retaining means to a disinfected writing utensil 16. The disinfected writing utensil 16 is expelled from an underside portion of the front panel 21 into the tray 24 succeeding proper sanitizing via a digit operated handle 52. In use, the handle 52 is rotated and the disinfected writing utensil 16 is expelled into the tray 24 for additional usage (also see FIG. 2).

The apparatus 10 also comprises a removable attachable lid 30 which further comprises a slot 31 which provides an opening for depositing the contaminated writing utensil 15. The lid 30 is envisioned to be attached to an upper portion of the enclosure 20 via interference fitting means, yet other attachment means may also be utilized without limiting the scope of the apparatus 10. The lid 30 also comprises a barricade 32 which provides a means to block a sterilizing light 60 from exiting the slot 31 and being seen by a user (see FIG. 2). The lid 30 is envisioned to be fabricated from materials such as, but not limited to: plastic, metal, or the like.

Referring now to FIG. 2, another perspective view of the apparatus 10, according to the preferred embodiment of the present invention, is disclosed. The apparatus 10 is depicted herein with the front panel 21 removed for illustration purposes only; it is known that said front panel 21 would be integrally attached to the enclosure 20 to prohibit the light 60 from being viewed by the user. As depicted herein, the lid 30 comprises an arcuate barricade 32 which is utilized to block the light 60 from exiting the slot 31. The barricade 32 is envisioned to be integrally molded to an underside surface of the lid 30 and is positioned in such as fashion as to obstruct the light 60. The barricade 32 is fabricated from a material similar to the lid 30. In use, it is also envisioned for the lid 30 to be removed from the enclosure 20 to access the light 60 for replacement as needed. An internal portion of the enclosure 20 comprises a guide panel 40, a rolling dispenser 50, and a light 60. The guide panel 40 is envisioned to be an arcuate surface which guides the contaminated writing utensil 15 downwardly passing beneath the light 60. The guide panel 40 routes the contaminated writing utensil 15 to the rolling dispenser 50 which enables a user to extract the disinfected writing utensil 16 from the internal portion of the enclosure 20. The guide panel 40 is envisioned to be integrally molded into the rear panel 22, yet other attachment means may be incorporated without limiting the scope of the apparatus 10. The rolling dispenser 50 comprises a longitudinally positioned groove 51 which accepts the disinfected writing utensil 16. The rolling dispenser 50 is manipulated via the handle 52 which protrudes from a side panel 23 and is rotated to rotate the groove 51 and the disinfected writing utensil 16 downwardly toward the tray 24 and drop said disinfected writing utensil 16 into said tray 24. The rolling dispenser 50 comprises a cylindrical-shape which is envisioned to be rotatably attached to each side panel 23.

The light 60 provides a means to sterilize the contaminated writing utensil 15. The light 60 is preferably an ultraviolet C (UVC) cold cathode illuminating source which is utilized as a germicide, yet other illuminating sources with similar characteristics may be utilized without limiting the scope of the apparatus 10. The light 60 is attached to an upper surface of a side panel 23, yet other locations may be utilized. As the contaminated writing utensil 15 rolls past the light 60 the wavelengths that said light 60 emits eradicates microorganisms on said contaminated writing utensil 15 which produces a disinfected writing utensil 16. The light 60 is attached to the power cord 61 and provides a digit-operated ON/OFF means to the light 60. The switch 62 is envisioned to comprise a common thumb-wheel switching means, yet other switching means may be utilized without limiting the scope of the apparatus 10.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little to no training. After initial purchase or acquisition of the apparatus 10, it would be installed as indicated in FIG. 1.

The method of utilizing the apparatus 10 may be achieved by performing the following steps: acquiring the apparatus 10; positioning the apparatus 10 on a level surface; inserting the power cord 61 into an existing circuit; activating the switch 62 to illuminate the light 60; positioning a contaminated writing utensil 15 into the slot 31; enabling the contaminated writing utensil 15 to roll on the guide panel 40 and roll pass the light 60, thereby sterilizing said contaminated writing utensil 15; rotating the handle 52 to enable the disinfected writing utensil 16 into the tray 24; retrieving the disinfected writing utensil 16 as desired; utilizing the apparatus 10 as desired; removing the lid 30 as necessary to replace the light 60; and enabling the apparatus 10 to sterilize and clean publicly used writing utensils in a manner that is quick, easy, and effective.

The foregoing descriptions of specific embodiments of the present invention have been presented to limit the invention to the precise forms disclosed, and obviously many modifications and variations are possible in light of the above teaching. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An Ultraviolet Disinfecting Apparatus for disinfecting contaminated writing utensils, said apparatus comprising:
   an enclosure having a front panel, a rear panel, a pair of opposing side panels, and an open top end;
   a lid removeably attached to said open top end, said lid having a slot for receiving a contaminated writing utensil;
   a guide panel housed within said enclosure, said guide panel having a curved profile;
   an ultraviolet light source housed within said enclosure and adjacent to said guide panel for disinfecting said contaminated writing utensil;

a power cord attached to said ultraviolet light source through said side panel; an ON/OFF switch attached to said power cord;

a barricade integrally molded to the underside of said lid positioned in a fashion to obstruct said ultraviolet light source and block said ultraviolet light source from being viewed by the user;

a tray disposed below said enclosure for receiving a contaminated writing utensil;

a rolling dispenser rotationally attached to said pair of side panels within said housing, said dispenser having a groove for receiving a disinfected writing utensil and a handle for rotating said dispenser and releasing said disinfected writing utensil into said tray.

2. A method of disinfecting a plurality of contaminated writing utensils utilizing an ultraviolet disinfecting apparatus of claim 1, said method comprising the steps of providing said ultraviolet disinfecting apparatus of claim 1;

placing said ultraviolet disinfecting apparatus of claim 1 on a level surface;

plugging said power cord of said ultraviolet disinfecting apparatus of claim 1 into an electrical outlet;

turning on said ultraviolet disinfecting apparatus of claim 1 with said ON/OFF switch;

inserting at least one contaminated writing utensil within said ultraviolet disinfecting apparatus of claim 1;

rotating said handle attached to said rolling dispenser of claim 1;

and, receiving a disinfected writing utensil from said tray of Ultraviolet disinfecting apparatus of claim 1.

* * * * *